(12) United States Patent
Sweigers et al.

(10) Patent No.: US 11,311,032 B2
(45) Date of Patent: Apr. 26, 2022

(54) METHOD FOR INOCULATING YEAST INTO FRUIT JUICE

(75) Inventors: Jan Hendrik Sweigers, Fredensborg (DK); Annicka Bunte, Malmö (SE); Sylvester Holt, Frederiksberg C (DK); Mansour Badaki, Vanløse (DK)

(73) Assignee: CHR. HANSEN A/S, Hoersholm (DK)

( * ) Notice: Subject to any disclaimer, the term of this patent is extended or adjusted under 35 U.S.C. 154(b) by 1 day.

(21) Appl. No.: 13/695,026

(22) PCT Filed: Apr. 26, 2011

(86) PCT No.: PCT/EP2011/056557
§ 371 (c)(1),
(2), (4) Date: Oct. 27, 2012

(87) PCT Pub. No.: WO2011/134952
PCT Pub. Date: Nov. 3, 2011

(65) Prior Publication Data
US 2013/0045301 A1    Feb. 21, 2013

(30) Foreign Application Priority Data
Apr. 27, 2010 (EP) .................................. 10161158

(51) Int. Cl.
| | | |
|---|---|---|
| C12G 1/022 | (2006.01) | |
| C12C 11/00 | (2006.01) | |
| A23L 2/02 | (2006.01) | |
| A23L 2/38 | (2021.01) | |
| A23L 2/52 | (2006.01) | |
| A23L 2/84 | (2006.01) | |
| C12N 1/04 | (2006.01) | |
| C12G 3/024 | (2019.01) | |

(52) U.S. Cl.
CPC ........ *A23L 2/02* (2013.01); *A23L 2/38* (2013.01); *A23L 2/52* (2013.01); *A23L 2/84* (2013.01); *C12G 1/0203* (2013.01); *C12G 3/024* (2019.02); *C12N 1/04* (2013.01)

(58) Field of Classification Search
CPC .. C12N 1/18; C12G 1/064; C12G 3/02; A23L 2/38
USPC ......... 426/590, 592, 62, 15, 16, 11, 51, 599, 426/650; 435/255.2, 255.1, 254.21, 435/255.21
See application file for complete search history.

(56) References Cited

U.S. PATENT DOCUMENTS

| | | | |
|---|---|---|---|
| 5,116,943 A * | 5/1992 | Koths et al. ................. | 530/351 |
| 5,427,943 A | 6/1995 | Suoranta | |
| 9,175,257 B2 | 11/2015 | Colavizza et al. | |
| 2006/0177543 A1 | 8/2006 | Tanaka | |
| 2018/0179479 A1 | 6/2018 | Bjerre et al. | |

FOREIGN PATENT DOCUMENTS

| | | |
|---|---|---|
| CA | 1299435 C | 4/1992 |
| CN | 1816616 | 8/2006 |
| CN | 1819776 | 8/2006 |
| DE | 36 25 170 C1 | 7/1987 |
| EP | 0 237 427 A2 | 9/1987 |
| EP | 1441027 A1 | 7/2004 |
| EP | 1645198 | 4/2006 |
| EP | 2090647 | 8/2009 |
| EP | 2 236 615 A1 | 10/2010 |
| JP | H09-037759 A | 2/1997 |
| JP | 2003-180339 A | 7/2003 |
| JP | 2008-506410 A | 3/2008 |
| RU | 2 092 083 C1 | 10/1997 |
| RU | 2 200 758 C1 | 3/2003 |
| RU | 2 207 139 C2 | 6/2003 |
| SU | 848475 A1 | 7/1981 |
| SU | 1104149 A1 | 7/1984 |
| WO | WO 91/12315 A1 | 8/1991 |
| WO | WO 99/40896 A1 | 8/1999 |
| WO | WO 00/39281 A2 | 7/2000 |
| WO | WO 01/70935 A2 | 9/2001 |
| WO | WO 2004/072271 A1 | 8/2004 |
| WO | WO 2005/003327 A1 | 1/2005 |
| WO | WO2006/008245 A1 | 1/2006 |
| WO | WO 2008/049232 A1 | 5/2008 |
| WO | WO 2008/065491 A2 | 6/2008 |
| WO | 2009/095137 | 8/2009 |
| WO | WO 2009/110807 A1 | 9/2009 |
| WO | WO-2016/193465 A1 | 12/2016 |

OTHER PUBLICATIONS

N.P. Jolly et al. The Role and Use of Non-*Saccharomyces* Yeasts in Wine Production, s. Afr. J. EnoL Vitie., vol. 27, No. 1, 2006 pp. 15-39.*
http://web.archive.org/web/20030103025315/http://www.botany.hawaii.edu/faculty/wong/Bot135/Lect14.htm Role of Yeast in Production of Alcoholic Beverages Jan. 3, 2003.*
http://www.homebrewtalk.com/showthread.php?t=16307 Home Brew Forums > Wine, Mead, Cider, Sake & Soda > Winemaking Forum > What are the Main Differences Between Wine and Beer Making? Nov. 12, 2006.*
[No Author Listed] Joy of Baking.com. "Yeast" JoyofBaking.com. Available online since Aug. 11, 2003. Last accessed via http://www.ioyofbaking.com/Yeast.html on Jan. 24, 2014.
No Author Listed] Lesaffre.com. "Yeast Baking." LeSaffre. Available since Jan. 25, 2008. Last accessed via http://www.lesaffre.com/en/yeast-baking/yeasts/frozen-yeasts.html on Jan. 24, 2014.
New Zealand Office Action, for Application No. 603267, dated Jan. 13, 2014.

(Continued)

*Primary Examiner* — Vera Stulii
(74) *Attorney, Agent, or Firm* — Foley & Lardner LLP

(57) ABSTRACT

The present invention provides a new wine yeast product in a frozen form. The product is produced in a fermenter, concentrated, cryoprotectants are added. This mixture is then frozen at −50° C. What makes this product unique is that besides the fact that it is frozen, it can be directly added to grape juice as no rehydration is required because the yeast was not dehydrated in the production process.

16 Claims, 1 Drawing Sheet

(56) References Cited

OTHER PUBLICATIONS

Figure 1:
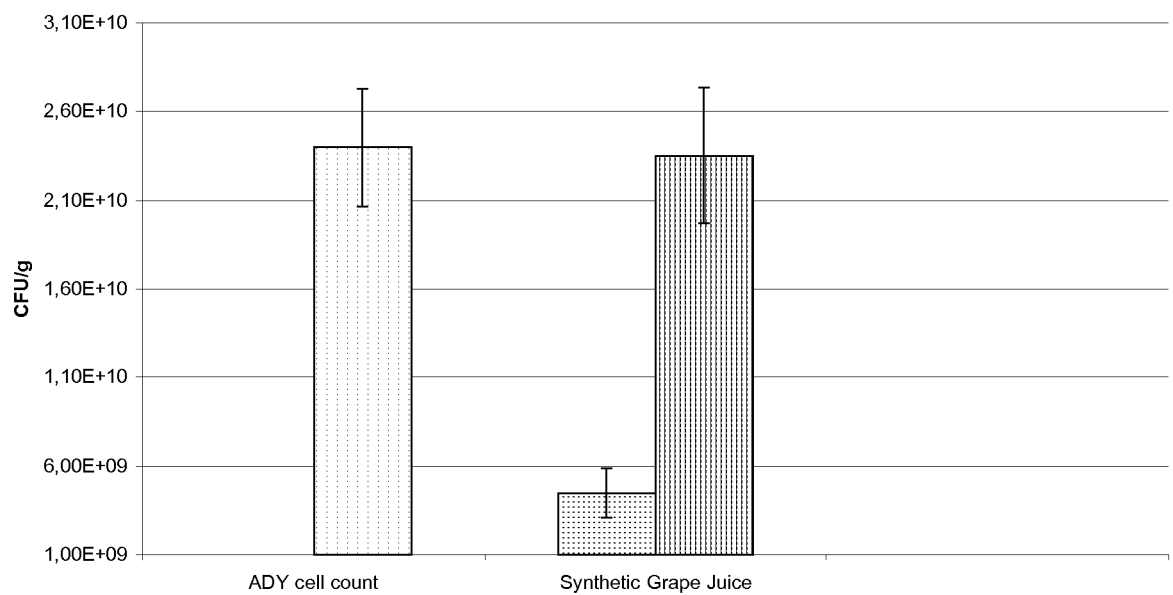

Gietz et al., Frozen competent yeast cells that can be transformed with high efficiency using the LiAc/SS carrier DNA/PEG method. Nature Protocol. 2007;2(1):1-4.
Nadal et al., Analysis and dynamics of the chromosomal complements of wild sparkling-wine yeast strains. Appl Environ Microbiol. 1999;65(4):1688-95.
Japanese Office Communication dated Sep. 18, 2014 for Application No. JP 2013-506628.
Adams, The Use of Stored Frozen Yeast Starter in Wine Production. Dev Ind Microbiol. 1962;3:341-6.
First Examination Report from NZ603267, dated May 8, 2013.
Office Action from CN201180021014.6, dated Jul. 16, 2013.
Bennetts, Dow Corning Corp. Application, 1974, RPC 235.
Blendax-Werke's Application, 1980, RPC 491.
*British Celanese Ltd.* v. *Courtaulds, Ltd*. 52, RPC 171.
Chen, T., "Manufacturing and application of microbial media", The First Edition, The First Page, China Agriculture Press.
Freshney, I., :Basic Principles of Cell Culture, Culture of Cells for Tissue Engineering, 2006, pp. 3-22, Freshneyhistologia.ugr.es/pdf/0471629359.pdf (available since 2006).
L'Oreals Application, 1970, RPC 565.
London Rubber Industries Ltd. Patent, Reports of Patent, Design and Trade Mark Cases, 1968, RPC 31.
So, J., "Corning Understanding and Managing Cell Culture Contamination", Life Sciences, wikisites.mcgill.ca/djgroup/images/9/9d/Contamination_%26_cell_line_mixed_up.pdf (available since 2007).
Tie, H. et al., "Assessment in frozen umbilical cord stem cells by controlled rate freezing", Medical Equipment, 9(6), pp. 12-13.
International Search Report from PCT/EP2011/0566557, dated Jul. 6, 2011.
International Preliminary Report on Patentability from PCT/EP2011/0566557, dated Aug. 29, 2012.
Iland et al., Monitoring the winemaking process from grapes to wine techniques and concepts. Patrick Hand Wine Promotions PTY Ltd., Australia. 2004:67.
Office Communication dated Jun. 26, 2015 for Japanese Application No. 2013-506628.
Office Communication dated Jun. 10, 2015 for Russian Application No. 2012150430.
Adams, The Use of Stored Frozen Yeast Starter in Wine Production. Developments in Industrial Microbiology. 1962;3:341-6.
Suzuki, Storage Technique for Yeasts (1) Method for Storing Yeasts. Microbiol. Cult. Coll. 2009;25(2):89-91.
Office Communication dated Apr. 14, 2015 for Russian Application No. RU 2012150430.
Costello, P.J., et al., "Standardised methodology for testing malolactic bacteria and wine yeast compatibility," Australian Journal of Grape and Wine Research 9; pp. 127-137, Jul. 2003.
Boulton, R. B., et al., Principles and Practices of Winemaking 124 (1996).
O'Kennedy, K.; "How to avoid stuck fermentations"; The Australian & New Zealand Grapegrower & Winemaker, 538: 103-105 (Nov. 2008).
Soubeyrand, V., et al., "Rehydration Protocols for Active Dry Wine Yeasts and the Search for Early Indicators of Yeast Activity," American Journal of Enology and Viticulture. 57:4 474-480 (Dec. 2006).
Coutinho, C., et al., "Trehalose as cryoprotectant for preservation of yeast strains," Journal of Biotechnology, 7: 23-32 (Jan. 1988).
Diniz-Mendes, L., et al., "Preservation of Frozen Yeast Cells by Trehalose," Biotechnology and Bioengineering, 65: 572-578 (Dec. 1999).
Moor H., et al., "Fine Structure in Frozen-Etched Yeast Cells," The Journal of Cell Biology, 17 ; 609-628 (Jun. 1963).
Lewis J.G., et al., "Role of Growth Phase and Ethanol in Freeze-Thaw Stress Resistance of *Saccharomyces cerevisiae*," Applied and Environmental Microbiology, 59: 1065-1071 (Apr. 1993).

Bauer, F. F., et al., "Yeast Stress Response and Fermentation Efficiency: How to Survive the Making of Wine—A Review," South African Journal for Enology and Viticulture, 21(Special Issue): 27-51 (2000).
PCT International Search Report in application No. PCT/EP2011/056557 dated Jul. 6, 2011.
PCT International Preliminary Report on Patentability in application No. PCT/EP2011/056557 dated Aug. 29, 2012.
Gallone et al., "Domestication and Divergence of *Saccharomyces cerevisiae* Beer Yeasts," Cell, vol. 166, pp. 1397-1410, Sep. 2016.
Swiegers et al., "The development of yeast strains as tools for adjusting the flavor of fermented beverages to market specifications," Biotechnology in Flavor Production: A Case-based Approach, Havkin-Frenkel and Belanger, eds., Chapter 1, pp. 1-55, 2008.
Adams, "Effect of Low Temperature ($-29°$ C.) on viability of Stored Starter," Report Horticultural Research Institute Ontario, *Studies on Storage Yeast III*, pp. 114-117 (1966).
Bouckley, "Chr. Hansen Pioneers First Frozen Yeast for Winemaking," FOODnavigator.com, 2 pages (Dec. 2010).
Wansbrough et al., "Chemistry in Winemaking," New Zealand Institute of Chemistry, http://nzic.org.nz/ChemProcesses/food/6B.pdf, 12 pages.
Definition of "wine". International Code of Oenological Practices, http://www.oiv.int/public/medias/3921/e-code-1-31.pdf, 2 pages (Jan. 2015).
Hui et al., "Handbook of Food and Beverage Fermentation Technology," Chap. 3, Table 9, p. 34 (Mar. 2004).
"New Frozen Yeast Released," The Australian & New Zealand Grapegrower & Winemaker, Issue 564, pp. 53-54 (Jan. 2011).
Oliver, "The Oxford Companion to Beer," Oxford University Press, p. 85 (2011).
Romano, et al., "Taxonomic and Ecological Diversity of Food and Beverage Yeasts," Table 2.1, p. 14, in Querol, et al. *Yeasts to Food and Beverage*, Springer Science & Business Media (2006).
Wellman, et al., "Storage of Brewing Yeasts by Liquid Nitrogen Refrigeration," *Applied Microbiology*, vol. 26, No. 4, pp. 577-583 (1973).
Yokoigawa, et al., "Simple Improvement in Freeze-tolerance of Bakers' Yeast with Poly-y-Glutamate," *Journal of Bioscience and Bioengineering*, vol. 102, No. 3, pp. 215-219 (2006).
Jermini, et al., "Infuence of Frozen Storage and Thaw-Freeze Stresses on the Viability of Osmotolerant Yeasts," *Journal of Food Protection*, vol. 50, No. 5, pp. 414-417 (1987).
Dictionary Le Nouveau Petit Robert, definitions of "Cidre", "Vin," "Biére," "Képhir," and "Saké," 5 pages (2002).
"Chr. Hansen Launches Frozen Yeast for Easy Wine-Making," Winebusiness.com, Nov. 29, 2010 (1 page).
"Chr. Hansen Launches Frozen Yeast for Easy Wine-Making," Nov. 30, 2010 (2 pages).
"Beer," Ullmann's Encyclopedia of Industrial Chemistry, Fifth, Completely Revised Edition, vol. A 3: Antidiabetic Drugs to Benzoquinone and Naphthoquinone Dyes, pp. 421-461 (1985).
"Wine," Ullmann's Encyclopedia of Industrial Chemistry, Fifth Completely Revised Edition, vol. A 28: Water to Zirconium and Zirconium Compounds (1996).
Breierova et al., "Cryoprotective Effects of Yeast Extracellular Polysaccharides and Glycoproteins", Cryobiology 29 (1992) 385-390.
Dumont et al., "Influence of cooling rate on *Saccharomyces cerevisiae* destruction during freezing: unexpected viability at ultra-rapid cooling rates", Cryobiology 46 (2003) 33-42.
Mazur et al., "Interactions of Cooling Velocity, Temperature, and Warming Velocity on the Survival of Frozen and Thawed Yeast," Cryobiology, vol. 5, No. 1, pp. 1-17 (1968).
Seki et al., "Intracellular ice formation in yeast cells vs. cooling rate: Predictions from modeling vs. experimental observations by differential scanning calorimetry," Cryobiology 58 (2009) 157-165.
Stewart, "Brewer's yeast propagation: The Basic Principles," MBAA TQ, vol. 54, No. 3, (2017) pp. 125-131.

\* cited by examiner

METHOD FOR INOCULATING YEAST INTO FRUIT JUICE

RELATED APPLICATIONS

This application is a U.S. National Stage application based on International Application No. PCT/EP2011/056557, filed Apr. 26, 2011, which claims priority to European Application No. EP10161158.0, filed Apr. 27, 2010, the contents of which are incorporated herein by reference in their entireties.

FIELD OF THE INVENTION

The present invention relates to a method for inoculating yeast into fruit juice or fruit. This is important for the beverage industry in general, especially for the wine industry.

BACKGROUND

For the last 50 years winemakers have become accustomed to inoculation their wine with pure cultures of yeast. Such inoculation cultures may also be termed "starter cultures". The yeast is in a dehydrated form called active dried yeast (ADY) which has been produced in fermenters, concentrated and then dried on a drum, a process called fluid bed drying. It may herein also be termed freeze-dried yeast.

As a result of the fact that the yeast is dehydrated, it therefore needs to be rehydrated, in order to be metabolically active, before application to the substrate such as grape juice as in the case of winemaking. This is a very delicate process for the yeast cells and requires a significant amount of attention and care to make sure that the yeast cell hydrates in a way that makes the cell viable.

As discussed on page 124, left column of the text book of Roger Boulton et al, 1996—during the drying process of active dried yeast production, the cellular membranes of the yeast cells loose their permeability barrier function. Therefore, to re-establish this function, it is important to re-hydrate the membranes by adding the yeast in water at 40° C. for 20 minutes. Therefore, the yeast re-hydration process typically involves a 20-30 minute rehydration in un-chlorinated water or a water/grape juice mix (2:1) between 35-38° C. then followed by the addition of grape juice of the same volume (50:50 juice/water blend) which is kept for another 20-30 minutes before adding it to wine. It is important that the grape juice should not contain any $SO_2$, which could kill the yeast cells during the sensitive process of rehydration (O'Kennedy, 2008). In addition, the rehydration mix must be cooled down with juice after 20 min in water, 5° C. at a time. Failure to cool down from the rehydration temperature after 30 minutes can also result in significant cell death (O'Kennedy, 2008). Furthermore, care should be taken to use uncontaminated grape juice for the rehydration protocol as rehydration with contaminated grape juice will result in contamination of all wine fermentation inoculated using the rehydration mixture. Different manufacturers propose variations on this protocol but the critical step is that dehydrated cells need to be exposed to water or a water/juice mixture at specific temperatures, conditions and for specific times in order to hydrate properly, thereby avoiding cell death and consequent in-activity. It is not recommended to add the active dried yeast directly to wine as the high sugar concentration, $SO_2$ and other compounds in grape juice do not allow for optimal rehydration of the yeast. For this reason, none of the wine yeast manufacturer proposes the direct inoculation of active dried yeast to grape must.

As known to the skilled person—in the present context the term fruit juice and fruit must are understood to be the same and these terms may herein be used interchangeably.

As described in Soubeyrand et al. 2006—active-dried yeast (freeze dried) loose activity when not optimally rehydrated. The incorrect rehydration of active dried yeast can also lead to stuck alcoholic fermentation (O'Kennedy, 2008). Therefore, the rehydration of active dried yeast needs a significant amount of time and concentration and usually demands a large number of skilled man-hours at a commercial winery during the winemaking process.

EP1645198A1 (Minaki Advance Co Ltd, Japan); EP2090647A1 (Chr. Hansen); and WO2009/095137A1 (Chr. Hansen) may be considered as herein relevant prior art.

However, none of these prior art documents discloses a method where yeast is added in frozen form to a fruit juice before fermentation.

The present invention relates to a novel method for inoculating yeast into fruit juice or fruit, whereby the above mentioned drawbacks can be avoided. The inventors have found that, surprisingly, a frozen culture (frozen starter culture) of yeast can be directly added to grape juice while maintaining a high level of survival rate of the yeast cells.

SUMMARY OF THE INVENTION

The present invention provides a new wine yeast product in a frozen form. The product is produced in a fermenter, concentrated, cryoprotectants are added. This mixture is then frozen at −50° C. in suitable containers. What makes this product unique is that besides the fact that it is frozen, is that it can be directly added to grape juice as no rehydration is required because the yeast was not dehydrated in the production process. The product is currently in the form of a frozen bag (plastic DIM bag) containing 1 kg of frozen yeast cell culture.

As shown in Example 1 herein—when directly inoculating frozen yeast, to the surprise of the present inventors, only a relatively small decrease in cell numbers was observed compared to active dried yeast where a much larger decrease in cell numbers where observed when directly inoculated compared to correct rehydration. Therefore, this feature makes the frozen yeast suitable for direct inoculation, a simple process where an unskilled person can open the container and directly add the contents to grape juice, without risking significant cell death and consequent loss of activity, as is the case for active dried yeast. Furthermore, direct inoculation of yeast prevents potential spoilage of wine fermentations by contaminated rehydration mixtures.

Accordingly, based on this surprising finding one can thereafter understand that the use of frozen yeast may be highly advantageous for wine production according to the present invention.

A further advantage is that direct inoculation results in a significant time and man-power savings for winemakers as rehydration of active dried yeast can take up to an hour and needs a skilled person preparing highly specified rehydration substrates and direct inoculation of frozen yeast takes a few minutes and does not need special training or skills, simply adding the product to the grape juice or crushed grapes.

The results provided herein have been obtained by using the wine yeast *Pichia kluyveri*. The skilled person may easily transfer the technology to other types of yeast, such as *Saccharomyces cerevisiae, Saccharomyces pastorianus,*

*Saccharomyces bayanus*, or *Torulaspora delbreuckii*, *Kluyveromyces thermotolerans* etc.

The product could also be applied to produce other beverages than wine such as beer, cider, sake, kefir, soft drinks and beverages where the action of the particular yeast is required and applied in a convenient, direct inoculation form. The starter culture may be used to ferment any type of sugar based medium, such as grape juice, or apple juice, or alternatively, whole fruits.

DRAWINGS

Figure 2:
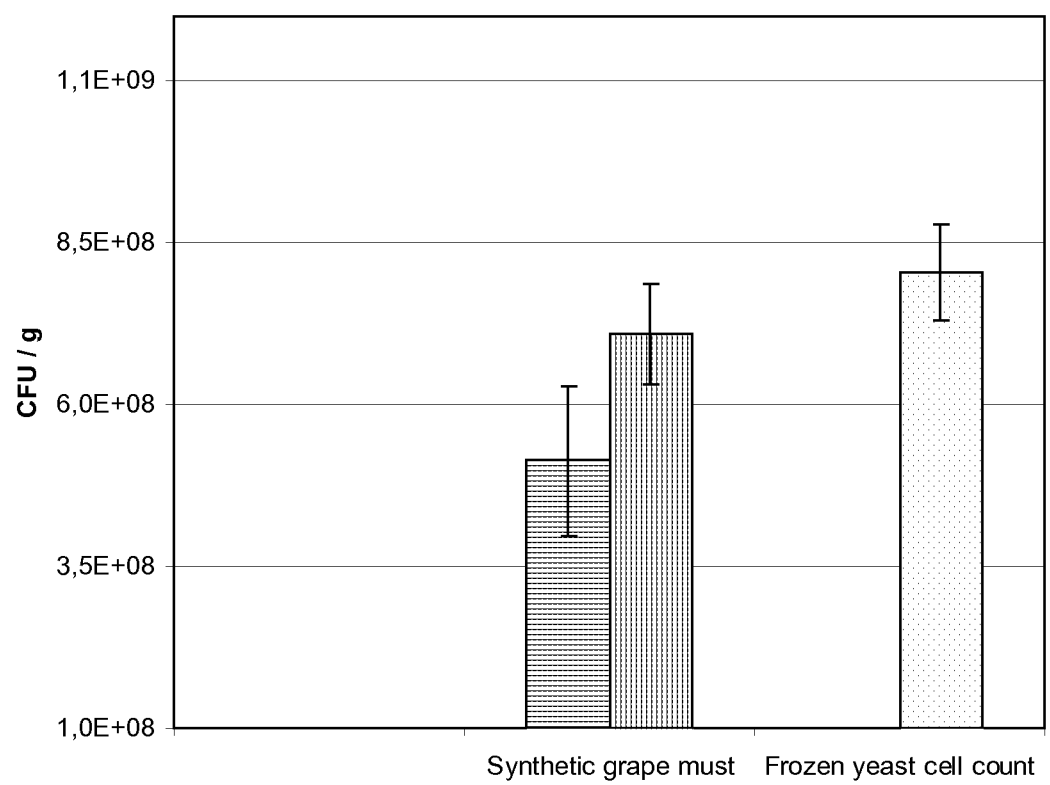

FIGS. 1 and 2: These figures show herein relevant experimental results as discussed in details in working Example 1 herein.

DETAILED DESCRIPTION

In one aspect, the present invention relates to a method for inoculating a yeast into a fruit juice or fruit. Said yeast will cause a fermentation, and the product of this fermentation may be used in the food industry, or more specifically the beverage industry. Beverages which are contemplated are e.g. wine, beer, cider or other beverages which are produced by way of fermenting a fruit or vegetable material, such as fruit juice, vegetables, plants or fruit. Examples of fruit or vegetable material are grapes, grape juice, apples or apple juice, or barley.

The yeast which is used may be any type of yeast which is used in the beverage or food industry. Examples include e.g. *Pichia kluyveri, Saccharomyces cerevisiae, Saccharomyces pastorianus, Saccharomyces bayanus, Torulaspora delbreuckii*, or *Kluyveromyces thermotolerans* etc.

It is common to use yeasts in the wine industry. Typical yeasts used in wine production are from the yeast family Saccharomycetaceae (ascomycetous yeasts). Yeasts from the genus *Saccharomyces* [e.g. the species *Saccharomyces cerevisiae* (SC)] are commonly used. Other used yeasts are from the same Saccharomycetaceae family but from other genera such as *Kluyveromyces* [e.g. the species *Kluyveromyces thermotolerans* (KT)] and the genus *Torulaspora* [e.g. the specie *Torulaspora delbrueckii* (TD)].

For the inoculation of fermenting a fruit or vegetable material, a pure yeast culture may be used (i.e. a culture containing only one type of yeast), but a mixed culture of two or more types of yeast may also be used as inoculant.

For a mixed starter culture it may be important to know the specific amount/ratio of each yeast species in the final commercially available starter culture. This is in particular true for a wine starter culture comprising *Saccharomyces* ssp., *Kluyveromyces* ssp. and/or *Torulaspora* ssp.

The starter culture may be produced by fermenting yeast, followed by harvesting the yeast by centrifugation. This produces a liquid yeast biomass. Typically, a 1000 L fermenter produces about 100 kg of "wet weight yeast" in the form of a liquid paste the liquid paste. Based on wet weight, this paste typically contains approximately $10^{10}$ CFU (colony forming units) per gram. After freezing, approximately $10^9$ CFU per gram remains.

To protect the cells from the harsh freezing conditions, a cryoprotectant may be added after or before centrifugation. Examples of cryopretectants include glucose, sucrose, trehalose.

Such cryoprotectants are typically added in an amount of about 5%-20%. The amount should be sufficient to maintain the number of CFU at approximately $10^9$ or above.

After adding cryoprotectant and collecting the liquid yeast biomass, the biomass is transferred to suitable container, e.g. plastic bags. These containers are then frozen at a temperature of between −10° C. and −60° C. A preferred temperature interval is between −10° C. and −30° C.

The method according to the invention entails adding the frozen starter culture to the sugar based medium in an amount which is sufficient to initiate and maintain fermentation of the vegetable material.

Accordingly, an aspect of the invention relates to a method for inoculating yeast into fruit juice comprising the following steps:
  a) providing a fruit juice in a container; and
  b) adding yeast in frozen form in an amount which is sufficient to initiate and maintain fermentation of the fruit juice.

The skilled would in the present context understand that when you add yeast in frozen form to the fruit juice according to step b) above—there is no herein rehydration of the yeast.

As understood by the skilled person—one may call the herein described method of the invention a direct inoculation method.

In working Example 1 is discussed experiments relating to the use of frozen yeast starter cultures for inoculation. Surprisingly, it was found that by thawing the frozen yeast culture before it was added to the grape juice, the survival of the cells (CFU/ml) in the grape juice was even better than what was achieved when directly inoculating the frozen yeast culture in the grape juice.

Accordingly, a separate aspect of the invention relates to a method for inoculating yeast into fruit juice comprising the following steps:
  i) providing a fruit juice in a container;
  ii) providing yeast in frozen form;
  iii) thawing the frozen yeast to get yeast in liquid form; and
  iv) adding the yeast in liquid form in an amount which is sufficient to initiate and maintain fermentation of the fruit juice.

The skilled person would in the present context understand that when one thaws the frozen yeast to get yeast in a liquid form and then add yeast in liquid form to the fruit juice according to step iii) above—there is no herein rehydration of the yeast.

As known to the skilled person—the temperature for the fermentation of the fruit juice step in a winery is typically between 15 to 25° C. Accordingly, when one in a winery adds yeast in frozen form to the fruit juice [i.e. according to step b) above] then is the yeast frozen form typically thawed at a temperature between 15 to 25° C.

In the working Example 1 herein was the thawing temperature 30° C.

Without being limited to theory—it is believed that one gets the herein best results by the thawing temperature of step iii) above being from 25 to 35° C.

As understood by the skilled person—the thawing of step iii) above may be done by e.g. adding the yeast in frozen form into e.g. water or a water juice mixture, wherein the water or a water juice mixture has a suitable temperature. As understood by the skilled person—one would thereby get yeast in liquid form that can be added to the fruit juice according to step iv) above.

EXAMPLES

Materials and Methods

The active dried yeast used in this example was *Saccharomyces bayanus* B52 (Lesaffre). The frozen yeast used in this example was *Pichia kluyveri* (Chr. Hansen). All inoculations were performed in triplicate, with the standard error indicated on the bar graphs in FIGS. 1 and 2 below. After inoculation with yeast, the mixture was agitated thoroughly to dissolve contents before making standard dilutions for plating. To determine the cell counts of these products, dilutions were made in peptone water and 1 ml poured into Petri-dishes after which Yeast Glucose Medium (YGM) agar was poured in liquid form at 40° C. Plates were incubated for 3 days at 30° C. after which colonies were counted. The CFU/g as indicated in FIGS. 1 and 2 below was calculated based on the original weight addition of ADY and frozen yeast.

To determine the cell counts of yeast after inoculation in synthetic grape juice medium, the same protocol was followed. An amount of 50 g/l of frozen or thawed *Pichia kluyveri* yeast was inoculated into 200 ml of synthetic grape juice medium at room temperature (21° C.). Active dried yeast was either rehydrated (20 min 37° C., 1 g in 10 ml of non-chlorinated water), or weighted out to perform direct inoculation with a 0.3 g/L, corresponding to $2*10^6$ CFU/ml. For direct inoculation and rehydrated ADY, the temperature of the synthetic grape must was adjusted to 30° C. to facilitate greater survival due to the temperature difference of the inoculum and media.

Synthetic grape must was prepared according to Costello et al. 2003 with a sugar concentration of 250 g/L and a pH of 3.5. After inoculation, dilutions were conducted in peptone water and 1 ml poured in Petri-dishes after which Yeast Glucose Medium (YGM) agar was poured in liquid form at 40° C. Plates were incubated for 3 days at 30° C. after which colonies were counted. Using the amount of yeast mass added to the synthetic grape must and the CFU/ml value obtained from the plate counts, a value in CFU/gram could be calculated.

Example 1

Use of Frozen Yeast—Comparison with Freeze-Dried Yeast

FIG. 1 shows the results of the detrimental effect of direct inoculation of active dried yeast (ADY) when directly inoculated in synthetic grape juice (horizontal lines) compared to first rehydrating the ADY yeast in water at 37° C. for 20 minutes and then inoculating it in synthetic grape must (vertical lines). After inoculation, cell counts were conducted by pour plating and the data used to calculate an average CFU/g value. The CFU/g of the original active dried yeast was on calculated on average as 2.40E+10 (dotted). Direct inoculation of the active dried yeast resulted in calculated average CFU/g value of 4.49E+9 meaning that 81.3% of the cells died due to direct inoculation. However, when first rehydrated in water at 37° C. for 20 mins and then inoculated in synthetic grape juice, the calculated average CFU/g was 2.35E+10 meaning that only about 2.1% of the cells died after rehydration and inoculation.

FIG. 2 shows the effect of direct inoculation of frozen yeast in synthetic grape must with and without thawing first. The cell count of the original frozen yeast product 8.0E+8 (dotted). After direct inoculation of frozen yeast (without thawing) in grape juice the cell count was calculated on average 5.1E+8 (horizontal lines) and after thawing then direct inoculating in grape juice the cell count was calculated on average 7.1E+8 (vertical lines) meaning that in the frozen direct inoculation (without thawing) only 36.3% of cells died and in the frozen direct inoculation (after thawing) only 11.3% of the cells died. This compares very favourably to the active dried yeast, where 81.3% of the cells died, indicating that frozen yeast can be used for direct inoculation without a significant loss in cell count and consequent activity.

CONCLUSIONS

The results of this Example 1 indicate that active-dried yeast (freeze dried) looses a significant amount of viable cells when directly inoculated (without re-hydration) compared to inoculation after re-hydration in water (specific temperature) and juice dilution—i.e. these results were in agreement with the prior art knowledge as discussed above.

However, when directly inoculated frozen yeast is used, to the surprise of the present inventors only a relatively small decrease in cell numbers was observed as in the case above.

Accordingly, based of this surprising finding one can thereafter understand that use of frozen yeast may be highly advantageous for wine production according to the present invention.

A further advantage is that direct inoculation results in a significant time saving for winemakers as rehydration of active dried yeast can take more than an hour and direct inoculation of frozen yeast takes a few minutes.

As indicated in the example above, surprisingly, it has been found that by first thawing the frozen culture and then directly inoculating in grape juice, the survival of the cells (CFU/ml) was even better than what is achieved when directly inoculating the frozen yeast culture in grape juice without thawing first.

REFERENCES

1. EP 1645 198
2. EP 2090 647
3. WO 2009/095137
4. Peter Costello, Paul Henschke and Andrew Markides (2003) Standardised methodology for testing malolactic bacteria and wine yeast compatibility. Australian Journal of Grape and Wine Research 9 (2): 127-137.
5. Roger Boulton, Vernon Singleton, Linda Bisson and Ralph Kunkee. 1996. Principles and Practices of Winemaking pp. 124.
6. Karien O'Kennedy. (2008). How to avoid stuck fermentations, The Australian & New Zealand Grapegrower & Winemaker. November, Issue 538, 103-105.
7. Virginie Soubeyrand, Anne Julien and Jean-Marie Sablayrolles (2006) Rehydration Protocols for Active Dry Wine Yeasts and the Search for Early Indicators of Yeast Activity American Journal of Enology and Viticulture. 57(4)-474-480.

The invention claimed is:

1. A method for producing beer comprising:
   (a) thawing frozen viable yeast to obtain thawed viable yeast in liquid form that has not been dehydrated or rehydrated, wherein the yeast is of a species selected from *Pichia kluyveri, Saccharomyces cerevisiae, Saccharomyces pastorianus*, and *Saccharomyces bayanus;*
   (b) inoculating the thawed viable yeast in liquid form that has not been dehydrated or rehydrated into a barley-based medium by direct inoculation of an amount sufficient to initiate and maintain fermentation of the barley-based medium, and
   (c) fermenting the yeast in the barley-based medium, to thereby produce beer.

2. The method of claim 1, wherein the yeast is of the species *Pichia kluyveri*.

3. The method of claim 1, wherein the yeast is of a species selected from *Saccharomyces cerevisiae, Saccharomyces pastorianus*, and *Saccharomyces bayanus*.

4. The method of claim 1, wherein step (b) comprises inoculating at least $10^9$ CFU/gram of the thawed viable yeast in liquid form.

5. The method of claim 1, wherein the frozen viable yeast is obtained by a process comprising (i) fermenting a yeast, (ii) harvesting the fermented yeast by centrifugation, and (iii) freezing the harvested yeast.

6. The method of claim 1, wherein the frozen viable yeast is in a mixture composition that comprises a cryoprotectant.

7. The method of claim 1, wherein the frozen viable yeast is in a composition that comprises a cryoprotectant in an amount of from 5 to 20% w/w.

8. The method of claim 5, wherein the freezing comprises freezing the harvested yeast with a cryoprotectant.

9. The method of claim 5, wherein the freezing comprises freezing the harvested yeast at a temperature of between −10° C. and −60° C.

10. The method of claim 5, wherein the freezing comprises freezing the harvested yeast at a temperature of between −10° C. and −30° C.

11. The method of claim 1, wherein, prior to step (a), the frozen viable yeast is obtained by a process comprising (i) fermenting a yeast, (ii) harvesting the fermented yeast by centrifugation, and (iii) freezing the harvested yeast.

12. The method of claim 11, wherein the freezing comprises freezing the harvested yeast with a cryoprotectant.

13. The method of claim 11, wherein the freezing comprises freezing the harvested yeast at a temperature of between −10° C. and −60° C.

14. The method of claim 11, wherein the freezing comprises freezing the harvested yeast at a temperature of between −10° C. and −30° C.

15. The method of claim 1, wherein the frozen viable yeast is in a composition that comprises the yeast in an amount of a least $10^9$ CFU per gram of the composition.

16. The method of claim 1, wherein the yeast is of the species *Saccharomyces pastorianus*.

* * * * *

UNITED STATES PATENT AND TRADEMARK OFFICE
CERTIFICATE OF CORRECTION

| | | |
|---|---|---|
| PATENT NO. | : 11,311,032 B2 | Page 1 of 1 |
| APPLICATION NO. | : 13/695026 | |
| DATED | : April 26, 2022 | |
| INVENTOR(S) | : Sweigers et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 113 days.

Signed and Sealed this
Tenth Day of June, 2025

Coke Morgan Stewart
*Acting Director of the United States Patent and Trademark Office*